United States Patent [19]

Lee, Sr. et al.

[11] Patent Number: 5,360,020

[45] Date of Patent: Nov. 1, 1994

[54] PIN SITE SHIELD RETAINER

[75] Inventors: Harry E. Lee, Sr., Paris, Tenn.; Harry E. Lee, Jr., Southaven, Miss.

[73] Assignee: Memphis Orthopaedic Design, Inc., Memphis, Tenn.

[21] Appl. No.: 46,633

[22] Filed: Apr. 14, 1993

[51] Int. Cl.$^5$ .................... A61B 17/34; A61F 13/56
[52] U.S. Cl. ............................. 128/888; 24/563; 606/54
[58] Field of Search .............. 606/151, 158, 157, 86, 606/120, 53, 54, 96, 232; 128/888; 24/563, 329, 327, 339

[56] References Cited

U.S. PATENT DOCUMENTS

| | | | |
|---|---|---|---|
| 1,983,969 | 12/1934 | Davis | 606/120 |
| 2,586,758 | 2/1952 | Zerr | 24/327 |
| 3,171,408 | 3/1965 | Childs et al. | |
| 4,291,698 | 9/1981 | Fuchs et al. | 606/232 |
| 4,466,437 | 8/1984 | Dyck et al. | |
| 4,943,293 | 7/1990 | Lee, Jr. | 128/888 |

Primary Examiner—Tamara L. Graysay
Attorney, Agent, or Firm—Heiskell, Donelson, Bearman, Adams, Williams & Caldwell

[57] ABSTRACT

The pin site shield having a separate sponge and retainer removably securable to an orthopedic pin, wire, or similar implement. The retainer comprises a body having a slot form therein for receiving the orthopedic pin and a clamping member hingedly secured thereto. The clamping member is selectively moveable between open and closed positions, with interlocking surfaces on the body and clamping member engaging one another when the retainer is in its closed position to secure the retainer at its appropriate position on the pin. Protrusions on the body and clamping member allow installation of the retainer by squeezing the protrusions between a thumb and forefinger, with removal of the retainer being effected by spreading the protrusions apart.

4 Claims, 2 Drawing Sheets

1

PIN SITE SHIELD RETAINER

BACKGROUND OF THE INVENTION

1. Field of the Invention

This invention relates to orthopedic surgical devices and, more particularly, to an improved pin site shield retainer which may be easily installed and removed by the user.

2. Description of the Prior Art

Fixation of severely broken bones frequently requires the use of a plurality of surgical pins, wires, or similar implements inserted radially into the injured limb, with the distal ends protruding outwardly through the patient's skin. Such surgical implements, referred to generally as pins, may be integral components of complex fixation systems, and may remain in position for several days, weeks, or even months, depending upon the severity of the injury and other factors. In order to minimize the risk of infection, it is essential that antiseptics be regularly applied to the point of entry of each surgical pin through the patient's skin. Maintaining an antiseptic barrier at the pin site has become a recognized problem in the industry.

U.S. Pat. No. 4,943,293 issued Jul. 24, 1990, to Lee, Jr., discloses a pin site shield which attempts to solve the aforementioned problem. The Lee apparatus comprises a surgical sponge containing a suitable liquid antiseptic, permanently attached to a collar which is removably securable to a surgical pin by means of a set screw. This apparatus effectively maintains antiseptic in the desired area, but suffers from at least two disadvantages. First, the collar is unacceptably difficult to install and remove for replacement by the patient, since the set screw is rather small and difficult to manipulate, particularly when the device is located in an area that is barely accessible. This problem is accentuated if the set screw is inadvertently removed from the collar, and must be located and reinserted into the threaded hole. Second, the Lee apparatus does not allow replacement of the sponge without replacing the collar as well, resulting in waste and unnecessary expense for the patient. While the sponges must be replaced on a regular basis, a single collar could be reused repeatedly if the sponges and collars were not fixed as a unit.

SUMMARY OF THE INVENTION

An object of the present invention is to provide a mechanism for securing an antiseptic sponge to a pin site, while overcoming the disadvantages of known pin site shields.

Specifically, an object of this invention is to provide a retainer for use with an antiseptic sponge which may be easily installed and removed by the patient.

A further object is to provide such a retainer which may be installed and removed, using only one hand.

Another object of this invention is to provide a retainer which allows replacement of the underlying antiseptic sponge, but may be used repeatedly with a plurality of sponges.

In order to achieve the above stated objects, the present invention comprises a clamping retainer which is removably securable to a surgical pin, wire, or similar implement, for retaining an antiseptic sponge in the vicinity of the point of entry. The retainer consists of a body having a slot formed therein for receiving the surgical implement, and a clamping member hingedly secured within a cavity in the body. The clamping member is pivotable between open and closed positions, so that a surgical pin may be inserted radially through the slot in the body with the clamping member in its open position and retained therein upon moving the clamping member to its closed position.

DETAILED DESCRIPTION OF THE PREFERRED EMBODIMENT

Figure 1:
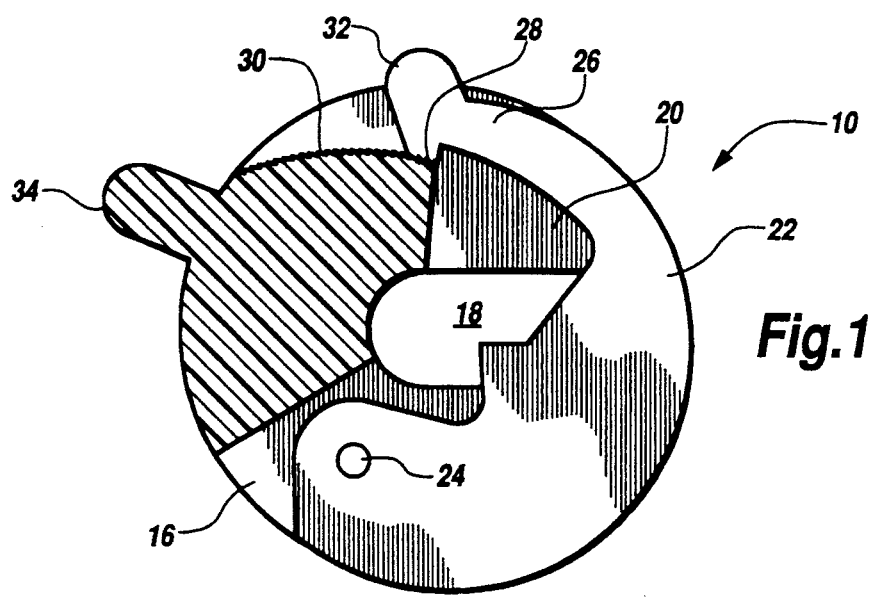
FIG. 1 is a side sectional view of the retainer of the present invention.
Figure 2:
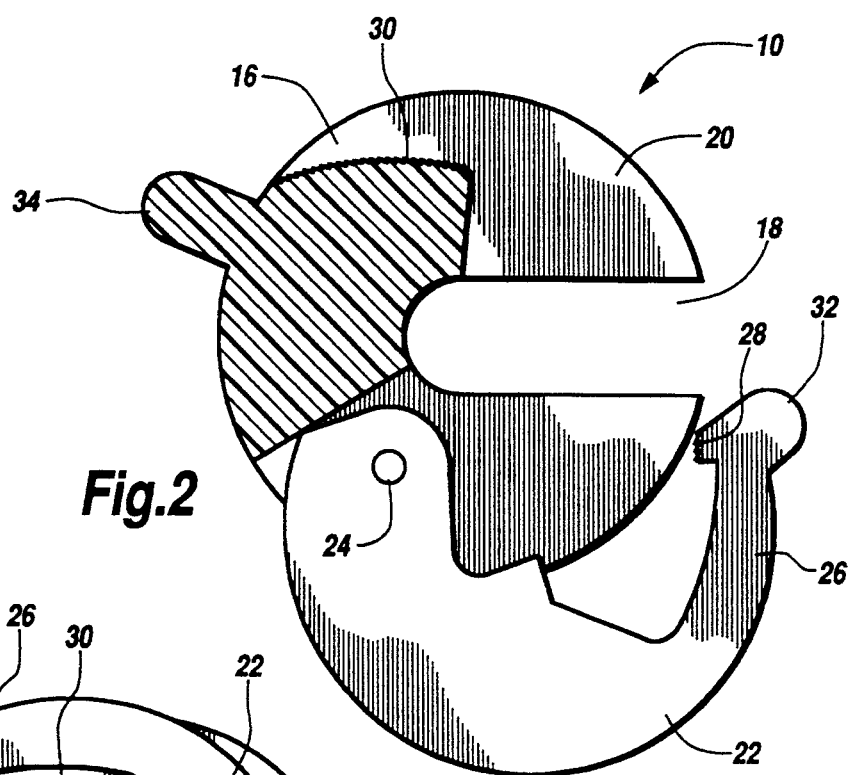
FIG. 2 is a side sectional view similar to FIG. 1, showing the retainer in its open position.
Figure 3:
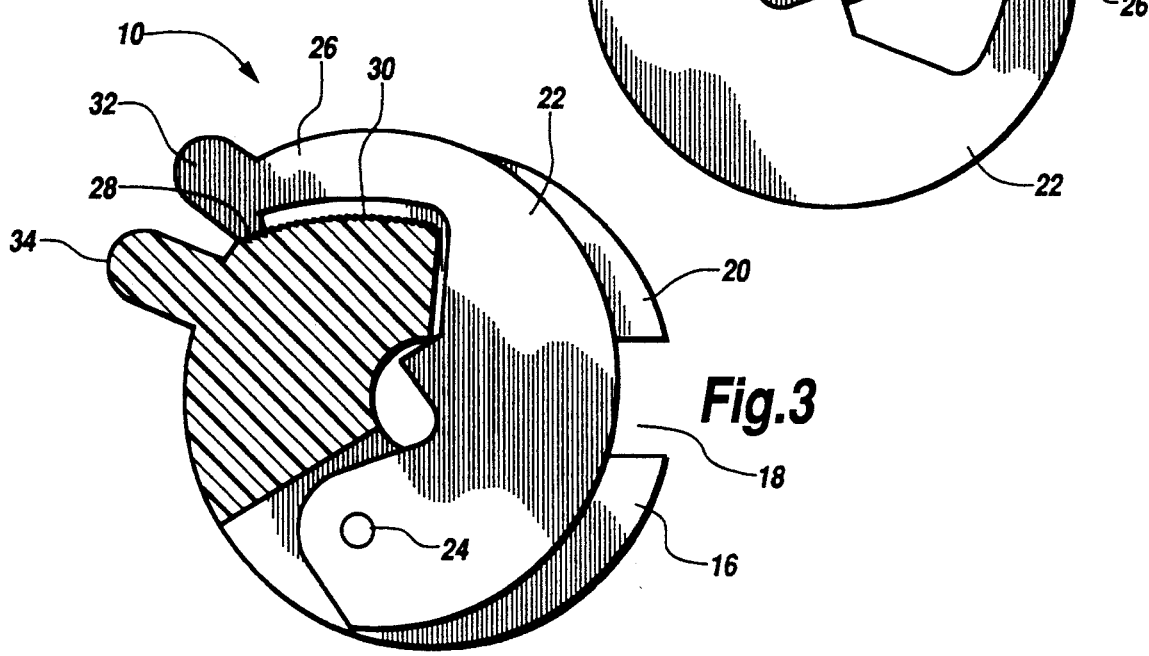
FIG. 3 is a side sectional view similar to FIGS. 1 and 2, showing the retainer in its fully closed position.
Figure 4:
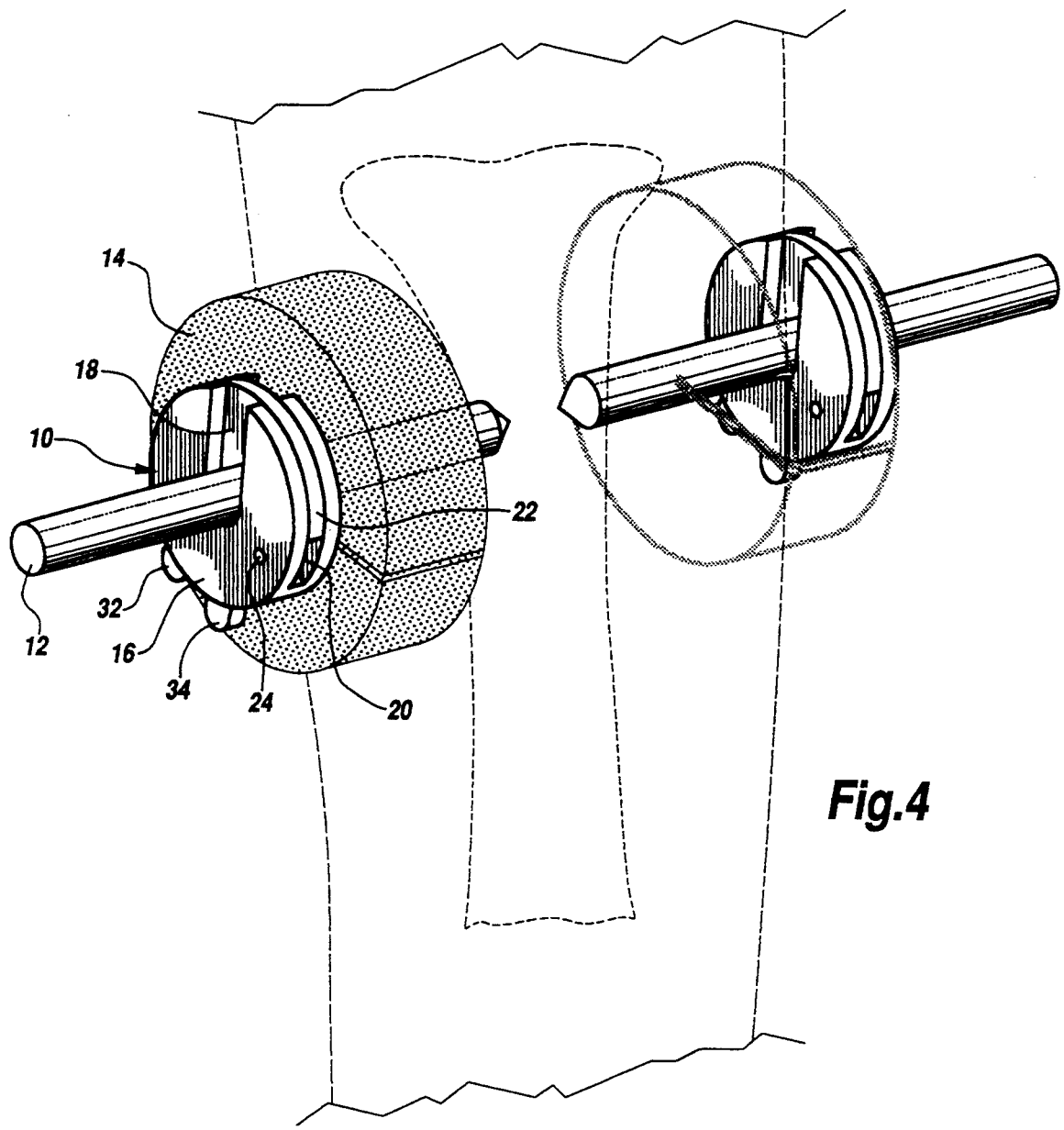
FIG. 4 is a perspective view showing a pair of retainers and surgical sponges attached to a surgical wire in a typical setting.

FIGS. 1 through 3 illustrate the preferred embodiment of a retainer 10 in accordance with the teachings of the present invention. In FIG. 4, retainer 10 is shown installed on a typical tension wire 12 to retain surgical sponge 14 adjacent to the point of entry. It is to be understood that FIG. 4 illustrates a typical usage for retainer 10, and that retainer 10 is equally well-suited for use with other orthopaedic fixation implements, particularly surgical pins. Those skilled in the art will appreciate the advantages provided by retainer 10 regardless of the setting in which it is used.

Retainer 10 consists of a disk-shaped body 16, having a radial slot 18 formed therein. Slot 18 is adapted to receive wire 12, so that retainer 10 may be easily positioned as desired. Body 16 further includes an internal cavity 20 with clamping member 22 pivotally mounted therein. As best illustrated in FIGS. 1–3, clamping member 22 is freely pivotable about hinge pin 24 within cavity 20 between open and closed positions as described more fully below.

Distal end 26 of clamping member 22 has an inwardly-facing serrated surface 28 formed thereon. Body 16 includes an outwardly-facing serrated surface 30 formed within cavity 20, which operatively engages serrated surface 28 upon moving clamping member 22 to its closed position shown in FIGS. 1 and 3. Serrated surfaces 28 and 30 are specifically configured to interlock, thereby retaining clamping member 22 in its closed position and preventing inadvertent loosening of retainer 10.

Distal end 26 of clamping member 22 also includes an outwardly-projecting protrusion 32 formed thereon. Body 16 has a similar protrusion 34 extending therefrom which, together with protrusion 32, may be conveniently grasped between the thumb and forefinger of a user's hand to move clamping member 22 from its open position to its closed position. The frictional engagement between serrated surfaces 28 and 30 facilitates securing retainer 10 at the appropriate position along the length of wire 12, thereby maintaining sponge 14 firmly against the point of entry. Retainer 10 may also be loosened, or removed entirely, simply by spreading apart protrusions 32 and 34 to move clamping member 22 towards its open position. When retainer 10 is formed of nylon or other suitable plastic material, the resiliency of the serrations in serrated surfaces 28 and 30 and in distal end 26 of clamping member 22 enhances the ability to open and close retainer 10 as desired by the user.

It will be fully appreciated by those skilled in the art that retainer 10 provides several unique advantages over previously known devices. As described above, initial installation of retainer 10 is easily accomplished by positioning body 16 as desired with wire 12 disposed within slot 18, and squeezing clamping member 22 to its closed position so that wire 12 is firmly gripped within slot 18. Replacement of sponge 14 only requires spreading protrusions 32 and 34 to remove retainer 10 so that sponge 14 may be accessed. In many instances, it may not be necessary to remove retainer 10 in order to replace sponge 14, since it is frequently possible to loosen clamping member 22 sufficiently to allow retainer 10 to be moved longitudinally along wire 12 without completely disengaging serrated surfaces 28 and 30. The ability to adjust retainer 10 without removing it will depend primarily on the diameter of wire 12, or whatever implement to which retainer 10 is attached. As shown in FIGS. 1 and 3, retainer 10 is adapted to be utilized with a plurality of orthopaedic devices having a variety of diameters.

As mentioned above, FIG. 4 depicts retainer 10 in a typical setting. The illustration of sponge 14 is to be understood as being by way of example only, since the configuration of the antiseptic sponge for purposes of the present invention is largely irrelevant.

While the principles of a retainer for use as a pin site shield have been clearly disclosed in the foregoing detailed description, it is to be understood that the embodiment disclosed herein is for illustrative purposes only, and that the scope of this invention is to be limited only by the appended claims.

What is claimed is:

1. A retainer for securing an antiseptic sponge at the point of entry for an orthopedic implement, removably securable to said implement adjacent said sponge, comprising:

a body having a slot formed therein for receiving said implement, said body comprising a disc-shaped member having an internal cavity formed therein and an access opening through an annular portion thereof, said slot being oriented substantially radially and intersecting said cavity, said cavity having a first interlocking surface formed thereon;

a clamping member having a proximate end hingedly secured to said body within said cavity and a distal end extending arcuately therefrom, said distal end having a second interlocking surface formed thereon, said clamping member being selectively moveable between open and closed positions; wherein movement of said clamping member to said closed position operatively closes said slot in said body, thereby compressively securing said implement within said slot, said first and second interlocking surfaces frictionally engaging one another to maintain said retainer in said closed position.

2. A retainer as set forth in claim 1, wherein:
   said body and said clamping members each have a finger engaging protrusion extending therefrom, thereby enabling a user to move said clamping member to said closed position by squeezing said protrusions between the thumb and finger of one hand.

3. A retainer as set forth in claim 2, wherein:
   said finger engaging protrusions are further adapted to enable the user to move said second clamping member to said open position.

4. A retainer as set forth in claim 1, wherein:
   said clamping member comprises a crescent-shaped member hingedly secured within said cavity in said body and substantially filling said access opening when in said closed position.

* * * * *